(12) United States Patent  
Merz et al.

(10) Patent No.: US 9,304,306 B2  
(45) Date of Patent: Apr. 5, 2016

(54) OPTICAL IMAGING SYSTEM

(71) Applicant: Carl Zeiss Meditec AG, Jena (DE)

(72) Inventors: Franz Merz, Aalen (DE); Artur Hoegele, Oberkochen (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/498,483

(22) Filed: Sep. 26, 2014

(65) Prior Publication Data

US 2015/0085358 A1    Mar. 26, 2015

(30) Foreign Application Priority Data

Sep. 26, 2013  (DE) .......................... 10 2013 219 383

(51) Int. Cl.  
G02B 21/00  (2006.01)  
A61B 3/12  (2006.01)  
G02B 21/02  (2006.01)  
G02B 21/22  (2006.01)

(52) U.S. Cl.  
CPC .............. G02B 21/0012 (2013.01); A61B 3/12 (2013.01); G02B 21/02 (2013.01); G02B 21/22 (2013.01)

(58) Field of Classification Search  
CPC .... G02B 21/0012; G02B 21/02; G02B 21/22; A61B 3/12  
USPC .......................... 359/376, 379, 381, 656–661  
See application file for complete search history.

(56) References Cited

U.S. PATENT DOCUMENTS

| 3,883,231 A * | 5/1975 | Koizumi ........................ 359/660 |
| 4,518,231 A | 5/1985 | Muchel et al. |
| 6,598,972 B2 | 7/2003 | Strahle |
| 6,788,455 B2 | 9/2004 | Kirchhuebel et al. |
| 6,943,942 B2 | 9/2005 | Horiguchi et al. |
| 6,967,774 B2 | 11/2005 | Kirchhuebel et al. |
| 7,085,046 B2 | 8/2006 | Horiguchi et al. |
| 7,408,705 B2 | 8/2008 | Horiguchi et al. |
| 7,570,408 B2 * | 8/2009 | Higuchi ..................... 359/221.1 |
| 7,791,794 B2 | 9/2010 | Reimer et al. |
| 7,839,494 B2 | 11/2010 | Reimer et al. |
| 8,023,120 B2 | 9/2011 | Reimer et al. |
| 2005/0012992 A1 * | 1/2005 | Kitajima ........................ 359/381 |
| 2005/0190436 A1 * | 9/2005 | Terada et al. ................. 359/381 |

FOREIGN PATENT DOCUMENTS

| DE | 35 39 009 A1 | 5/1987 |
| DE | 94 15 219.5 U1 | 11/1994 |
| DE | 10 2010 018 123 A1 | 10/2011 |

* cited by examiner

*Primary Examiner* — Frank Font  
(74) *Attorney, Agent, or Firm* — Walter Ottesen P.A.

(57) ABSTRACT

An optical imaging system generates an image of an object plane and includes a lens system which, in turn, includes a main objective and a reduction optical unit between the main objective and the object plane. The reduction optical unit includes a first composite element with a positive refractive power and a second composite element with a negative refractive power. The first composite element includes a first and second lens. The second composite element includes a third and fourth lens. An object-side first main plane and an image-side second main plane are defined by the lens system. The optical imaging system defines an observation beam path which is guided through the lens system so that, in each of the first main plane and the second main plane, the observation beam path is at a distance from the optical axis of the lens system.

8 Claims, 3 Drawing Sheets

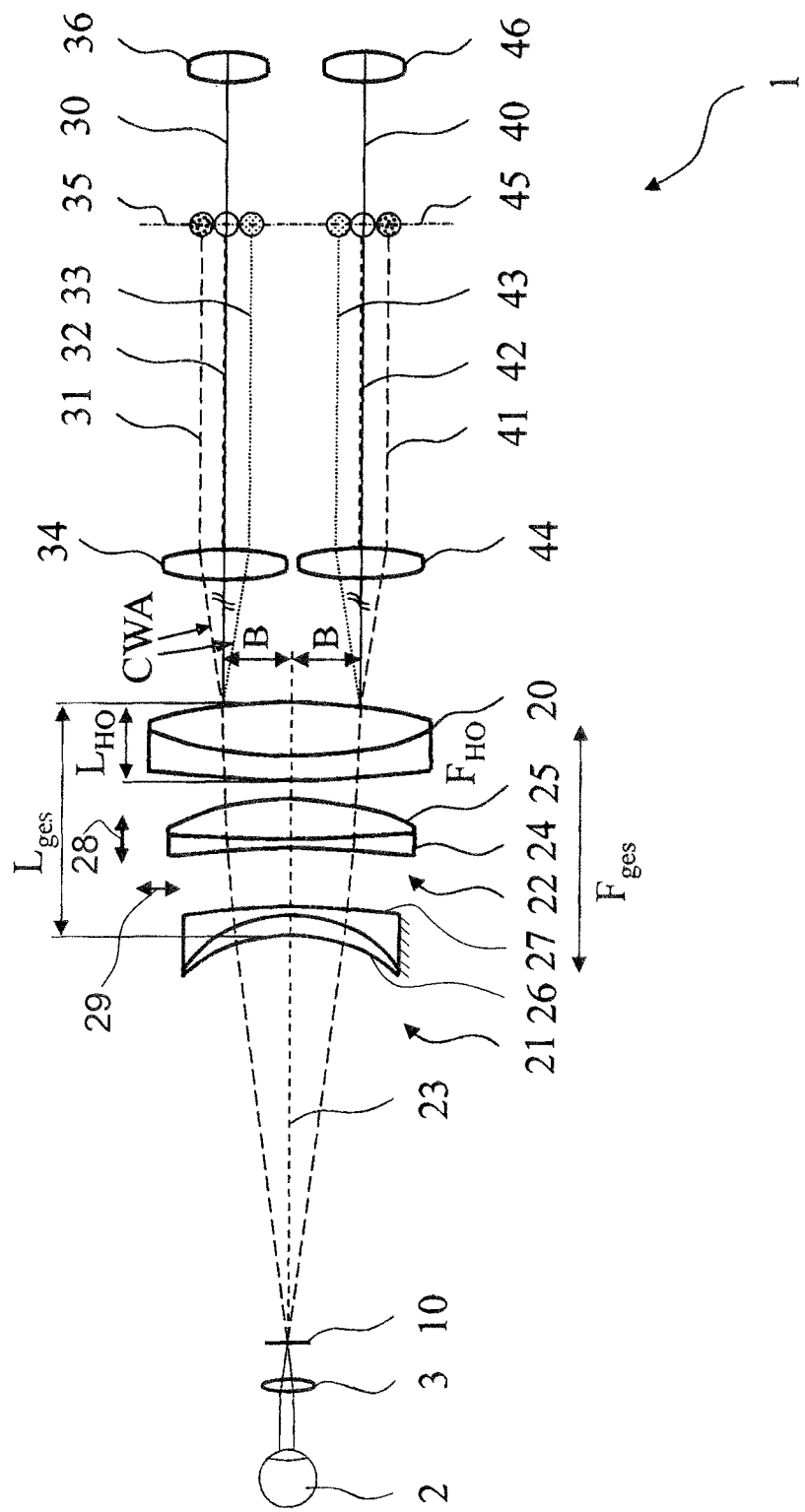

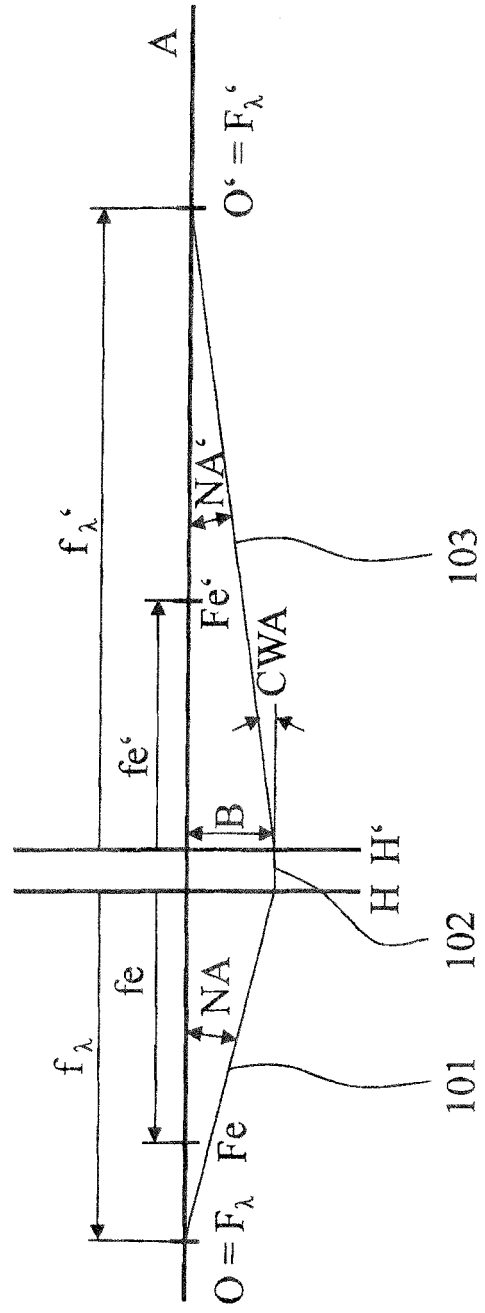

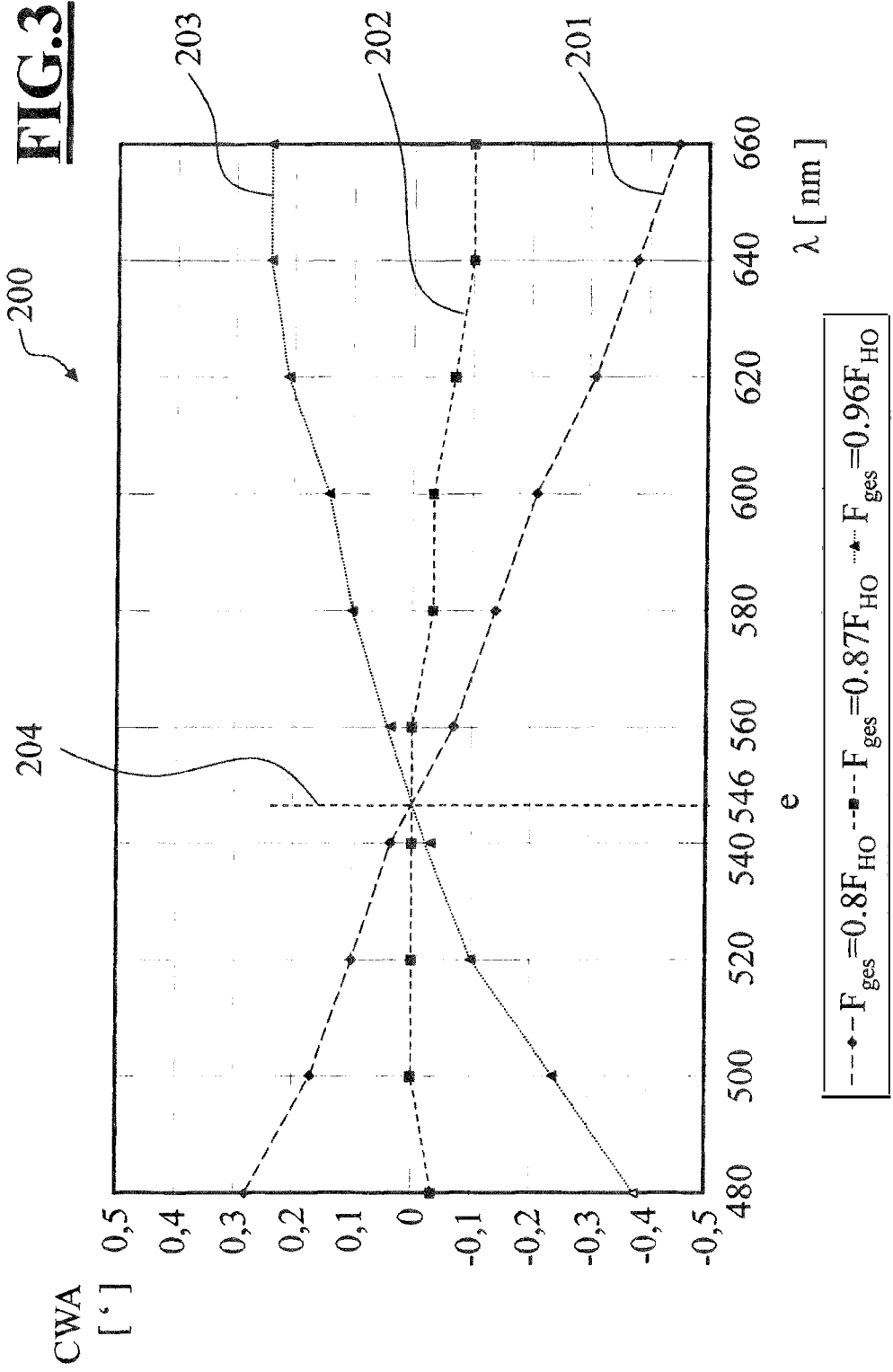

OPTICAL IMAGING SYSTEM

CROSS REFERENCE TO RELATED APPLICATION

This application claims priority of German patent application no. 10 2013 219 383.1, filed Sep. 26, 2013, the entire content of which is incorporated herein by reference.

FIELD OF THE INVENTION

The invention relates to an optical imaging system, in particular a microscope, for generating an image of an object plane, including a lens system which includes a main objective and a reduction optical unit between the main objective and the object plane and which is aligned along an optical axis. The reduction optical unit includes a first composite element with a positive refractive power and a second composite element with a negative refractive power. The first composite element is disposed between the main objective and the second composite element. The first composite element includes a first lens and a second lens. The second composite element includes a third lens and a fourth lens. An object-side first main plane and an image-side second main plane are defined by the lens system. The optical imaging system defines an observation beam path which is guided through the lens system in such a way that, in each of the first main plane and the second main plane, the observation beam path has a distance from the optical axis of the lens system.

When observing an object through an optical imaging system, in particular through a stereo surgical microscope, a wide angle optical unit can be introduced into the beam path between the main objective of the optical imaging system and the object to be observed, for example an eye. This enables observation of the fundus. In addition to this wide angle optical unit, a reduction optical unit can be pivoted into the beam path between the wide angle optical unit and the main objective of the optical imaging system in order to enable the adaptation of the wide angle optical unit to an optical imaging system, for example a surgical microscope.

BACKGROUND OF THE INVENTION

U.S. Pat. Nos. 6,788,455 and 6,967,774 have disclosed a microscope for wide angle observation for ophthalmic surgery which, by way of selectively addable optical units, allows an image of the fundus to be generated. The microscope includes a lens system, which includes a main objective and lenses disposed upstream of the main objective.

A disadvantage of this microscope is that the imaging quality in the wide angle observation is not ideal. As a result of the small distance between the main objective and the object to be observed, very short focal lengths result for a wide angle optical unit that can be added to the beam path. The wide angle optical unit can be adapted to the microscope via a further reduction optical unit which can be introduced into the beam path; however, this is linked to the disadvantage of a reduced imaging quality.

In addition to the optical disadvantages, the optical imaging system in accordance with U.S. Pat. Nos. 6,788,455 and 6,967,774 have a relatively long installation length. In order not to unnecessarily hinder the user, for example a surgeon, in his work with the optical imaging system on the object, for example a patient eye, a reduction optical unit should only have a short installation length and additionally be disposed as closely as possible to the main objective.

SUMMARY OF THE INVENTION

It is an object of the invention to provide an optical imaging system, in which a very high imaging quality is achieved when using a reduction optical unit upstream of a main objective. Furthermore, it is an object to provide an imaging system with a short installation length.

According to the invention, this object is achieved by virtue of the first lens (24) having a lower refractive power than the second lens (25) and the third lens (26) having a lower refractive power than the fourth lens (27). The first lens (24) is manufactured from a first material which has a first Abbe number, the second lens (25) is manufactured from a second material which has a second Abbe number, the third lens (26) is manufactured from a third material which has a third Abbe number and the fourth lens (27) is manufactured from a fourth material which has a fourth Abbe number. The first Abbe number is less than the second Abbe number and the third Abbe number is less than the fourth Abbe number. Here, the lens system is configured in such a way that the following relation is satisfied for a wavelength range $\lambda$ of 480 nm$\leq\lambda\leq$660 nm and for a main wavelength e=546 nm:

$$\left|\arctan\left(\frac{B}{f'_e + (f_e \cdot f'_e / (f_\lambda - f_e))}\right)\right| < 0.5',$$

where:
B=distance between an observation beam path and the optical axis in the first main plane H;
$f_e$=object-side focal length for the main wavelength e in respect of the first main plane H;
$f\lambda$=object-side focal length for the wavelength A in respect of the first main plane H;
$f_e'$=image-side focal length for the main wavelength e in respect of the second main plane H'.
The term "0.5'" has units of minutes of arc.

If the lens system is embodied in such a way that the following condition is satisfied for all wavelengths $\lambda$ between 480 nm and 660 nm and for a main wavelength e=546 nm $$\left|\arctan\left(\frac{B}{f'_e + (f_e \cdot f'_e / (f_\lambda - f_e))}\right)\right| < 0.5',$$

then the imaging quality for an observation beam path is so good that contrast-reducing and bothersome aberrations are corrected, and so an unchanging high contrast of the imaging and an unchanging high image quality are achieved over the whole wavelength range $\lambda$.

In one embodiment of the invention, the first material and the second material are selected in such a way that a difference between the first Abbe number and the second Abbe number lies between 27 and 36. The third and fourth materials are selected in such a way that a difference between the third and fourth Abbe numbers lies between 20 and 29.

When designing the lens system, it was found to be particularly advantageous to select the first material and the second material of the two lenses of the first composite element in such a way that the difference in the Abbe numbers of the two materials lies between 27 and 36. Furthermore, it is advantageous to select the third and the fourth material of the two lenses of the second composite element in such a way that the difference in the Abbe numbers of these two materials lies between 20 and 29. Using this, the described condition can be satisfied well and a very good contrast advantageously emerges over the whole wavelength range while having a low chromatic angle deviation.

In a further embodiment of the invention, the first material, the second material, the third material and the fourth material are selected in such a way that a first refractive index of the first material is greater than 1.55, a second refractive index of the second material is greater than 1.55, a refractive index of the third material is greater than 1.55 and a refractive index of the fourth material is greater than 1.55.

The aforementioned condition can be satisfied well by using materials with high refractive indices, that is greater than 1.55, for all lenses of the reduction optical unit including the two lenses of the first composite element and the two lenses of the second composite element. As a result, a well corrected image with a very good contrast and a low chromatic angle deviation advantageously emerges.

In a further embodiment of the invention, the first composite element is disposed in a stationary manner and the second composite element is disposed displaceably in the direction of the optical axis.

The distance of the object plane to be observed from the main objective may vary. As a result, it may be necessary to adapt the focus of the optical observation apparatus to the modified object plane. In order to allow the focus setting of the microscope to stay unchanged, it is advantageous if the reduction optical unit offers the option of focusing. This focusing option can be achieved relatively easily by virtue of the first composite element of the reduction optical unit being disposed in a stationary manner and the second composite element being able to perform a relative movement along the optical axis. With the optical imaging system of the invention, a good correction of the chromatic angle deviation is ensured over the whole focusing range.

In a further embodiment of the invention, the second composite element is disposed in a stationary manner and the first composite element is disposed displaceably in the direction of the optical axis.

The same advantages as described in the preceding embodiment can be achieved if the second composite element of the reduction optical unit is disposed in a stationary manner and the first composite element of the reduction optical unit is disposed displaceably in the direction of the optical axis.

In a further embodiment of the invention, the reduction optical unit can be pivoted into the beam path upstream of the main objective.

In order to enable the user of a microscope to work alternatively with or without the reduction optical unit, it is advantageous if the reduction optical unit can be simply introduced into the beam path or removed from the beam path. As a result, the user can quickly and easily switch back-and-forth between two focus planes without having to change the focus setting of the microscope. Advantageously, the reduction optical unit can be pivoted into and out of the beam path upstream of the main objective very easily and quickly via a pivoting device.

In a further embodiment of the invention, a further optical element for generating an intermediate image is fastened in the observation beam path upstream of the reduction optical unit and the optical imaging system is focused onto the intermediate image.

A further optical element can be introduced into the beam path upstream of the reduction optical unit. The observed object plane can then constitute an intermediate image plane, which emerges spatially in the beam path between the further optical element and the reduction optical unit. Deficiencies in the imaging quality resulting from the introduction of the further optical element can particularly advantageously be corrected chromatically by the reduction optical unit such that a very good high-contrast image without image offset can be observed.

In a further embodiment of the invention, the optical imaging system is embodied as a stereo microscope which includes a first observation beam path and a second observation beam path, wherein, in the first main plane H and in the second main plane H', the first and the second observation beam paths each have a distance B from the optical axis of the lens system.

The lenses of the reduction optical unit are usually embodied in a rotationally symmetric manner with respect to the optical axis. As a result of the optical axis of the main objective and the optical axis of the reduction optical unit being identical, the optical chromatic correction for all observation beam paths extending at a distance B from the optical axis with respect to the two main planes H and H' is equally good. For a stereo microscope, an advantage emerging from this is that both observation beam paths are corrected equally well chromatically by a single reduction optical unit. This advantage also applies to each further observation beam path guided at a distance B from the optical axis in respect of the two main planes H and H'.

BRIEF DESCRIPTION OF THE DRAWINGS

The invention will now be described with reference to the drawings wherein:

FIG. 1 shows a first embodiment of an optical imaging system according to the invention, including a reduction optical unit mounted upstream of a main objective;

FIG. 2 shows a schematic of a beam path in an optical imaging system in accordance with FIG. 1; and, FIG. 3 shows an image-side chromatic angle deviation in relation to a wavelength of between 480 nm and 660 nm for three different focal lengths of the optical imaging system in accordance with FIG. 1.

DESCRIPTION OF THE PREFERRED EMBODIMENTS OF THE INVENTION

FIG. 1 depicts an exemplary embodiment of an optical imaging system 1 according to the invention, including a reduction optical unit mounted upstream of a main objective 20.

The exemplary embodiment shows an optical imaging system 1 for observing an eye 2. The optical imaging system 1 is configured as a stereoscopic observation system with a right-hand observation beam path 30 and a left-hand observation beam path 40 and includes a main objective 20 with an optical axis 23, a right-hand tube lens 34, a left-hand tube lens 44 and a right-hand eyepiece 36 and a left-hand eyepiece 46. It may comprise further optical elements not depicted here.

A further optical element in the form of an ophthalmic lens 3 and a reduction optical unit have been introduced into the beam path between the main objective 20 and the eye 2. The reduction optical unit includes a first composite element 22 and a second composite element 21.

The first composite element 22 disposed directly upstream of the main objective 20 includes a first lens 24 and a second lens 25. The first lens 24 is embodied as a negative lens and has a negative refractive power. The second lens 25 is embodied as a positive lens and has a positive refractive power. The magnitude of the positive refractive power of the second lens 25 is greater than the magnitude of the negative refractive power of the first lens 24. Hence, the first composite element 22 is embodied as a lens combination with positive refractive power and has the effect of a positive lens.

The second composite element 21 includes a third lens 26 and a fourth lens 27. The third lens 26 is embodied as a positive lens and has a positive refractive power. The fourth lens 27 is embodied as a negative lens and has a negative refractive power. The magnitude of the negative refractive power of the fourth lens 27 is greater than the magnitude of the positive refractive power of the third lens 26. As a result, the second composite element 21 is embodied as a lens combination with a negative refractive power and has the effect of a negative lens.

The right-hand observation beam path 30 and the left-hand observation beam path 40 pass through the ophthalmic lens 3 and may cross in an image plane 10. The right-hand observation beam path 30 emanating from the image plane 10 passes through the second composite element 21, which has the effect of a negative lens, the first composite element 22, which has the effect of a positive lens, the main objective 20, the right-hand tube lens 34 and reaches the right-hand eyepiece 36. Here, an eyepiece intermediate image, which can be observed through the right-hand eyepiece 36 by an observer, is generated in a right-hand eyepiece intermediate image plane 35 in the right-hand observation beam path 30. The left-hand observation beam path 40 emanating from the image plane 10 is guided through the second composite element 21, the first composite element 22, the main objective 20 and the left-hand tube lens 44 to the left-hand eyepiece 46. Here, an eyepiece intermediate image, which can be observed through the left-hand eyepiece 46 by an observer, is generated in a left-hand eyepiece intermediate image plane 45 in the left-hand observation beam path.

Downstream of the main objective 20, the right-hand observation beam path 30 extends parallel to the optical axis 23. This parallel distance is denoted by B. Accordingly, the left-hand observation beam path 40 likewise extends parallel to the optical axis 23 at a distance B downstream of the main objective 20. The parallel distance between the two observation beam paths (30, 40) downstream of the main objective 20 may also be referred to as a stereo base SB, wherein the stereo base SB has a value double that of the distance B. A typical numerical value for the stereo base SB may be 25 mm.

Typical values for the focal lengths of the ophthalmic lens 3 are 60 diopter, 90 diopter or 120 diopter. The short focal length of the ophthalmic lens 3 may be a cause for occurring aberrations, which are referred to as spectral tilting of the optical axes or as a chromatic angle deviation CWA.

FIG. 1 schematically shows the effects of the chromatic angle deviation CWA. The chromatic angle deviation CWA should be understood to mean a color-dependent chromatic image offset between the eyepiece intermediate images, perpendicular to the optical axis 23. Due to a symmetric design, the same values in terms of magnitude are to be expected for the chromatic angle deviation CWA of the right-hand observation beam path 30 and of the left-hand observation beam path 40. A chromatic angle deviation may also occur for a single observation beam path. Chromatic angle deviations for three wavelength ranges in the form of three component beams are depicted for the right-hand observation beam path 30: a right-hand red component beam 31, a right-hand green component beam 32 and a right-hand blue component beam 33. A chromatic angle deviation for three wave regions in the form of a left-hand red component beam 41, a left-hand green component beam 42 and a left-hand blue component beam 43 is depicted for the left-hand observation beam path 40. The image offset of the right-hand component beams (31, 32, 33) in the right-hand observation beam path 30 in a right-hand eyepiece intermediate image plane 35 is visible through the right-hand eyepiece 36. The image offset of the left-hand component beams (41, 42, 43) in the left-hand observation beam path 40 in a left-hand eyepiece intermediate image plane 45 is visible through the left-hand eyepiece 46.

Without chromatic correction, the image offset caused by the chromatic angle deviation CWA is perceived to be contrast-reducing and bothersome. If this chromatic image offset is above the resolution limit of the eye, the observer perceives colored double images. The green wavelength range, in the form of the green component beams (32, 42), is depicted in the center of the eyepieces. The blue image region in the form of the blue component beams (33, 43) is visible within the region between the two eyepiece centers. The red wavelength range, in the form of the red component beams (31, 41), is visible outside of the region between the eyepiece centers.

In this exemplary embodiment, the reduction optical unit, which includes the second composite element 21 and the first composite element 22, is disposed very closely to the main objective 20. The main objective 20 has a structural length $L_{HO}$. The thickness or extent of the main objective 20 along the optical axis 23 is referred to as structural length $L_{HO}$. An overall structural length $L_{ges}$ refers to the greatest extent of the main objective 20 and the reduction optical unit, which includes the first composite element 22 and the second composite element 21, in relation to the optical axis 23. By way of example, if the main objective 20 has a structural length $L_{HO}$=1 cm, $L_{ges}$<3.2 cm emerges for the overall structural length.

As a result of the very close arrangement of the reduction optical unit upstream of the main objective 20, the provision of a high-contrast, chromatically corrected image region with a very high imaging quality constitutes a particular challenge.

Reference should still be made to the fact that the image plane 10 depicted in this exemplary embodiment is represented as an intermediate image plane, in which the right-hand observation beam path 30 and the left-hand observation beam path cross. The image plane 10 may also constitute a different object plane to be observed. Likewise, the position of the first composite element 22 and the position of the second composite element 21 may be disposed in an interchanged manner.

FIG. 2 shows a schematic of a beam path of the optical imaging system 1 in accordance with FIG. 1.

An optical axis A is drawn as thick horizontal line. Perpendicular to the optical axis A, a first main plane H serves as reference plane for focal lengths or distance data in the object space and a second main plane H' serves as reference plane for the image space. The two main planes (H, H') render it possible to describe the effect of the complex optical lens system by the equation valid for a thin lens. The first main plane H and the second main plane H' are both defined perpendicular to the optical axis of the lens system and therefore extend parallel to one another. The two main planes (H, H') replace the main objective 20 and the reduction optical unit, which includes the first composite element 22 and the second composite element 21.

The optical lens system images an object point O on an image point O'. From the object point O, a first ray 101 extends to the first main plane H at an angle NA in relation to the optical axis A. The angle NA is also referred to as object-side numerical aperture. A second ray 102 extends parallel to the optical axis A between the first main plane H and the second main plane H'. In each of the first main plane H and the second main plane H', the second ray 102 is at a distance B from the optical axis A. In the case of a stereoscopic imaging system, B may have a value which, in terms of magnitude, corresponds to the numerical value of half of the stereo base SB. When emerging from the second main plane H', a third ray 103 is directed to the image point 0'. The third ray 103 includes an angle CWA with the optical axis A. The angle CWA represents the image-side chromatic angle deviation CWA. If the image-side chromatic angle deviation CWA equals zero, the image point O' lies at infinity.

For the object space, an object-side focus Fe has the object-side focal length fe for a main wavelength e. In the image space, the image-side focus Fe' has the image-side focal length fe' for the main wavelength e. Therefore, an object-side focal length fλ for an object-side focus O=Fλ and an image-side focal length fλ' for an image-side focus O'=Fλ' emerge conformally for a wavelength λ.

In order to solve the problem, it was found that the chromatic angle deviation CWA measure constitutes a very good option for evaluating measures for optimizing the image quality. Expediently, a main wavelength e=546 nm is assumed when calculating the optical unit. The main wavelength e is also referred to as Fraunhofer line e and defines the main wavelength in the green spectral range of the sun. In order to image an object point O, for example the image plane 10, with high contrast and a very good imaging quality, it is necessary to provide an optical unit which is chromatically corrected over the visible wavelength range λ between 480 nm and 660 mm.

The reduction optical unit, including the first composite element 22 and the second composite element 21, is disposed upstream of the main objective 20. The first composite element 22, disposed directly upstream of the main objective 20, includes the first lens 24 with a negative refractive power and the second lens 25 with a positive refractive power. The magnitude of the positive refractive power of the second lens 25 is greater than the magnitude of the negative refractive power of the first lens 24 so that the first composite element 22 acts as a positive lens. In order to achieve a very good achromatic effect, a material with a lower Abbe number is to be selected for the first lens 24 with a lower refractive power than for the second lens 25 with a higher refractive power. Here, the difference in the Abbe numbers preferably lies between 27 and 36.

The second composite element 21 includes the third lens 26 with a positive refractive power and the fourth lens 27 with a negative refractive power. The magnitude of the negative refractive power of the fourth lens 27 is greater than the magnitude of the positive refractive power of the third lens 26 so that the second composite element 21 acts as a negative lens. In order to achieve a high image quality, a material with a lower Abbe number is to be defined for the third lens 26 than for the fourth lens 27. In this case, the difference between the Abbe numbers preferably lies between 20 and 29.

Both the first lens 24 and the second lens 25 of the first composite element 22 and the third lens 26 and the fourth lens 27 of the second composite element 21 are preferably manufactured from a material having a high refractive index, preferably with a refractive index greater than or equal to 1.55. By using lenses with high refractive index, it is possible simultaneously to correct necessary corrections of the monochromatic image aberrations, such as spherical aberration, coma or astigmatism.

A very good high-contrast image quality is achieved if the color ranges of the right-hand component beams (31, 32, 33) of the right-hand observation beam path 30 and the color ranges of the left-hand component beams (41, 42, 43) of the left-hand observation beam path are in each case perceived to be congruent in the eyepiece intermediate image plane (35, 45). To this end, it is necessary for a chromatic angle deviation which is less than 0.5' to be achieved for all wavelength ranges of the visible light between 480 nm and 660 nm.

As shown in FIG. 2, the object-side and the image-side focal lengths of the optical system in respect of the two main planes H and H' are in each case dependent on the wavelength λ. Here, the following three focal lengths are important:
$f_e$=object-side focal length for the main wavelength e in respect of the first main plane H;
$f_\lambda$=object-side focal length for the wavelength λ in respect of the first main plane H;
$f_e'$=image-side focal length for the main wavelength e in respect of the second main plane H'.

If the lens system is embodied in such a way, that is if the reduction optical unit, which includes the first composite element 22 and the second composite element 21, and the main objective 20 are matched to one another in such a way, that the following relation is satisfied for a wavelength range λ of 480 nm≤λ≤660 nm and for a main wavelength e=546 nm:

$$\left| \arctan\left( \frac{B}{f_e' + (f_e \cdot f_e' / (f_\lambda - f_e))} \right) \right| < 0.5',$$

then the imaging quality for an observation beam path is corrected so well that an unchanging good contrast of the imaging and an unchanging, very good image quality over the whole wavelength range λ are achieved. As a result of this, the color ranges of the right-hand component beams (31, 32, 33) of the right-hand observation beam path 30 and the color ranges of the left-hand component beams (41, 42, 43) of the left-hand observation beam path are respectively perceived as being congruent in the eyepiece intermediate image plane (35, 45). As a result, a chromatic angle deviation which is less than 0.5' is achieved.

In one embodiment of the reduction optical unit, in which the above-described material conditions are satisfied for the first composite element 22 and the second composite element 21, it is possible to achieve a chromatic angle deviation which is less than 0.2 and for which the following therefore applies:

$$\left| \arctan\left( \frac{B}{f_e' + (f_e \cdot f_e' / (f_\lambda - f_e))} \right) \right| < 0.2'.$$

By way of example, for a wavelength λ=660 nm, the chromatic angle deviation CWA can be calculated as follows for the exemplary embodiment:
fe=−175.102 mm (for e=546 nm)
fe'=+175.102 mm (for e=546 nm)
fλ=−175.033 mm (for λ=660 nm)
B=12 mm.
Therefore, the following emerges for the CWA:

$$CWA = \left| \arctan\left( \frac{B}{fe' + (fe \cdot fe'/(f\lambda - fe))} \right) \right|$$

$$= \left| \arctan\left( \frac{12 \text{ mm}}{175.102 \text{ mm} + \left( \frac{-175.102 \text{ mm} \cdot 175.102 \text{ mm}/}{(-175.033 \text{ mm} - (-175.102 \text{ mm}))} \right)} \right) \right|$$

$$= 0.093'$$

Since 0.093'<0.5', the condition for good image quality with a low chromatic angle deviation CWA is satisfied for a wavelength λ=660 nm and a main wavelength e=546 nm.

If this condition is satisfied for all wavelengths λ between 480 nm and 660 nm, the selected material and form combination of the reduction optical unit, which includes the first composite element 22 with the effect of a positive lens and the second composite element 21 with the effect of a negative lens, is suitable for satisfying the object.

It is desirable for there to be no need for changing the focus setting of the microscope when the reduction optical unit is introduced into the observation beam paths (30, 40). To this end, it is advantageous if the reduction optical unit can change the focal length, that is focus onto the image plane 10. In the exemplary embodiment in FIG. 1, the overall focal length $F_{ges}$ of the optical system, which includes the main objective 20 and the reduction optical unit, is selected in such a way that it lies in the range between 0.7-times and 1.1-times the focal length of the main objective $F_{Ho}$. This value is sufficient to enable focusing on the image plane 10 by the reduction optical unit. To this end, the second composite element 21, which has the effect of a negative lens, is disposed in a stationary manner and the first composite element 22, which has the effect of a positive lens, is disposed in a displaceable manner along the optical axis 23. The displaceability is indicated by the double-headed arrow 28 above the first composite element 22 in FIG. 1. In an alternative embodiment, it is also possible for the first composite element 22, with the effect of a positive lens, to be disposed in a stationary manner and for the second composite element 21, with the effect of a negative lens, to be disposed in a displaceable manner along the optical axis 23. FIG. 1 shows a central focus setting with a focal length $F_{ges}=0.87*F_{HO}$.

The diagram in FIG. 3 shows a result for suitable material and form stipulation for the first composite element 22 and the second composite element 21 which, for the wavelengths of the visible light and various focus settings, supplies a chromatically corrected, high-contrast image.

FIG. 3 depicts an image-side chromatic angle deviation CWA in relation to a wavelength λ in the visible range between 480 nm and 660 nm for three different focal lengths of the first exemplary embodiment.

The diagram 200 shows the chromatic angle deviation CWA in minutes of arc on the Y-axis in a range from −0.5' to +0.5'. The X-axis plots the wavelength range λ between 480 nm and 660 nm. The main wavelength e=546 nm is highlighted by a dashed line 204. The chromatic angle deviation CWA is depicted for three focal lengths: a first focal length $F_{ges}=0.80*F_{HO}$ is depicted by a first curve 201; a second focal length $F_{ges}=0.87*F_{HO}$ is depicted by a second curve 202 and a third focal length $F_{ges}=0.96*F_{Ho}$ is depicted by a third curve 203. The first curve 201 and the third curve 203 in each case show the focus setting in a possible final position.

For the central focus setting with a focal length $F_{ges}=0.87*F_{HO}$, the image-side chromatic angle deviation CWA is corrected particularly well for the whole wavelength range λ0 between 480 nm and 660 nm, and lies in the range between −0.1' and zero, see the second curve 202. For the main wavelength e=546 nm, the chromatic angle deviation CWA equals zero.

The chromatic angle deviation CWA for a focus setting with the focal length $F_{ges}=0.80*F_{HO}$ lies in the range between +0.28' and −0.45' for the whole wavelength range λ between 480 nm and 660 nm, see the first curve 201. The chromatic angle deviation CWA also equals zero for the main wavelength e=546 nm in this focus setting.

The image-side chromatic angle deviation CWA for a focus setting with the focal length $F_{ges}=0.97*F_{HO}$ lies in the range between −0.39' and +0.24' for the whole wavelength range λ between 480 nm and 660 nm, see the third curve 203. The image-side chromatic angle deviation CWA also equals zero for the main wavelength e=546 nm in this focus setting.

The curves 201, 202 and 203 clearly show that the image-side chromatic angle deviation CWA lies in the range of +/−0.5' for all focal lengths over the whole focusing range.

Hence, an optical imaging system 1 is provided which, when using a reduction optical unit, which can be introduced into a beam path (30, 40), which can be focused and which includes a first composite element 22 with the effect of a positive lens and a second composite element 21 with the effect of a negative lens, achieves a very short installation length upstream of a main objective. This optical imaging system achieves a very good image quality over the whole focusing range while having a very low chromatic angle deviation.

In a further embodiment of the invention, the reduction optical unit (21, 22) can be pivoted into the beam path between the image plane 10 and the main objective 20. In order to enable the user of a microscope to work alternatively with or without the reduction optical unit, it is advantageous if the reduction optical unit can be simply introduced into the beam path or removed from the beam path as indicated by double arrow 29 in FIG. 1. As a result, the user can quickly and easily switch back-and-forth between two focus planes without having to change the focus setting of the microscope.

It is understood that the foregoing description is that of the preferred embodiments of the invention and that various changes and modifications may be made thereto without departing from the spirit and scope of the invention as defined in the appended claims.

LIST OF REFERENCE SIGNS

1 Optical imaging system
2 Eye
3 Ophthalmic lens
10 Image plane
20 Main objective
21 Second composite element
22 First composite element
23 Optical axis
24 First lens
25 Second lens
26 Third lens
27 Fourth lens
28 Double arrow indicating displaceability of the first composite element 22 along the optical axis
29 Double arrow indicating movability of the optical reduction unit (21, 22) into and out of beam path
30 Right-hand observation beam path
31 Right-hand red component beam
32 Right-hand green component beam
33 Right-hand blue component beam
34 Right-hand tube lens
35 Right-hand eyepiece intermediate image plane
36 Right-hand eyepiece
40 Left-hand observation beam path
41 Left-hand red component beam
42 Left-hand green component beam
43 Left-hand blue component beam
44 Left-hand tube lens
45 Left-hand eyepiece intermediate image plane
46 Left-hand eyepiece
101 First ray of the beam path from the object point O to the main plane H in the object space
102 Second ray of the beam path between the main planes H and H'

103 Third ray of the beam path from the main plane H' to the image point O' in the image space
200 Diagram of chromatic angle deviation CWA
201 First curve, CWA for $F_{ges}=0.80F_{HO}$
202 Second curve, CWA for $F_{ges}=0.87F_{HO}$
203 Third curve, CWA for $F_{ges}=0.96F_{HO}$
204 Dashed line, main wavelength e=546 nm

What is claimed is:

1. An optical imaging system for generating an image of an object plane, the optical imaging system defining an optical axis and comprising:
    a lens system including a main objective and a reduction optical unit arranged between said main objective and the object plane;
    said lens system being aligned along the optical axis;
    said reduction optical unit including a first composite element having a positive refractive power and a second composite element having a negative refractive power;
    said first composite element being disposed between said main objective and the second composite element;
    said first composite element includes a first lens and a second lens;
    said second composite element includes a third lens and a fourth lens;
    said lens system defining an object-side first main plane (H) and an image-side second main plane (H');
    the optical imaging system defining an observation beam path which is guided through the lens system so as to cause said observation beam path to be at a distance B from the optical axis of the lens system in each of said first main plane (H) and said second main plane (H');
    said first lens having a lower refractive power than said second lens and said third lens having a lower refractive power than said fourth lens;
    said first lens being manufactured from a first material having a first Abbe number; said second lens being manufactured from a second material having a second Abbe number; said third lens being manufactured from a third material having a third Abbe number; and, said fourth lens being manufactured from a fourth material having a fourth Abbe number;
    said first Abbe number being less than said second Abbe number and said third Abbe number being less than said fourth Abbe number; and,
    said lens system being configured so as to cause the following relation to be satisfied for a wavelength range ($\lambda$) of 480 nm$\leq\lambda\leq$660 nm and for a main wavelength e=546 nm:

$$\left|\arctan\left(\frac{B}{f_e' + (f_e \cdot f_e'/(f_\lambda - f_e))}\right)\right| < 0.5',$$

wherein:
    $f_e$=object-side focal length for the main wavelength (e) with respect to said first main plane (H);
    $f_\lambda$=object-side focal length for the wavelength ($\lambda$) with respect to said first main plane (H);
    $f_e'$=image-side focal length for the main wavelength (e) with respect to the second main plane (H').

2. The optical imaging system of claim 1, wherein: said first material and said second material are selected so as to cause a difference between said first Abbe number and said second Abbe number to lie between 27 and 36; and, said third and said fourth materials are selected so as to cause a difference between said third and fourth Abbe numbers to lie between 20 and 29.

3. The optical imaging system of claim 1, wherein:
    said first material has a first refractive index, said second material has a second refractive index, said third material has a third refractive index, and said fourth material has a fourth refractive index; and,
    said first material, said second material, said third material and said fourth material are selected so as to cause said first refractive index of the first material to be greater than 1.55, said second refractive index of the second material to be greater than 1.55, said refractive index of the third material to be greater than 1.55 and said refractive index of the fourth material to be greater than 1.55.

4. The optical imaging system of claim 1, wherein said first composite element is fixedly mounted and said second composite element is mounted so as to be displaceable in the direction of the optical axis.

5. The optical imaging system of claim 1, wherein said second composite element is fixedly mounted and the first composite element is mounted so as to be displaceable in the direction of the optical axis.

6. The optical imaging system of claim 1, wherein said reduction optical unit is configured to be pivotable into the beam path between said main objective and said object plane.

7. The optical imaging system of claim 1, further comprising:
    an additional optical element configured to generate an intermediate image being mounted in said observation beam path between said reduction optical unit and said object plane; and,
    said optical imaging system being focused onto said intermediate image.

8. The optical imaging system of claim 1, wherein:
    said optical imaging system is configured as a stereo microscope;
    said observation beam path includes a first observation beam path and a second observation beam path; and,
    said first and said second observation beam paths, in said first main plane (H) and in said second main plane (H'), each are at a distance (B) from the optical axis of said lens system.

* * * * *